Figure 2:
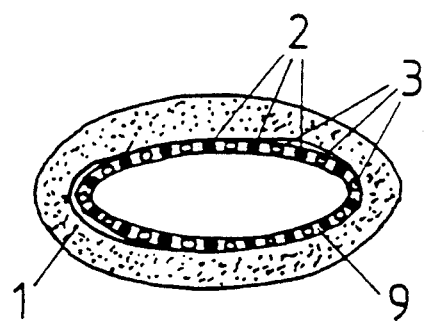

United States Patent [19]

Klaue

[11] Patent Number: 5,180,395
[45] Date of Patent: Jan. 19, 1993

[54] SELF-LOCKING BONE-SHAFT PART

[75] Inventor: Kaj Klaue, Neuenegg, Switzerland

[73] Assignee: Laboratorium für experimentelle Chirurgie, Davos, Switzerland

[21] Appl. No.: 459,791

[22] PCT Filed: Jun. 23, 1989

[86] PCT No.: PCT/CH89/00122
§ 371 Date: Feb. 21, 1990
§ 102(e) Date: Feb. 21, 1990

[87] PCT Pub. No.: WO90/00374
PCT Pub. Date: Jan. 25, 1990

[30] Foreign Application Priority Data

Jul. 5, 1988 [CH] Switzerland .................. 02559/88

[51] Int. Cl.$^5$ .............................................. A61F 2/34
[52] U.S. Cl. ........................................ 623/23; 623/16
[58] Field of Search .................. 623/1, 12, 13, 15, 16, 623/18, 22, 23

[56] References Cited

U.S. PATENT DOCUMENTS

| | | | |
|---|---|---|---|
| 3,893,196 | 7/1975 | Hochman | 623/23 |
| 4,441,215 | 4/1984 | Kaster | 623/1 |
| 4,459,708 | 7/1984 | Buttazzoni | 623/23 |
| 4,610,688 | 9/1986 | Silvestrini | 623/12 |
| 4,714,467 | 12/1987 | Lechner et al. | 623/18 |
| 4,750,905 | 6/1988 | Koeneman | 623/23 |

Primary Examiner—David Isabella
Attorney, Agent, or Firm—Walter C. Farley

[57] ABSTRACT

A shaft-part for a joint-end prosthesis or bone-shaft replacement and is implantable in a tubular bone 1, including a hollow, frusto-conical braid 5 constituted by two mutually crossing series of fibers 2, 3. When traction is exerted on the fibers 2, 3, the frusto-conical braid narrows; if, on the other hand, compression is exerted on the fibers 2, 3, the diameter of the frusto-conical braid 5 widens. These effects may be used on one hand to implant while the shaft rests areally against the marrow cavity 13 and on the other hand to remove the shaft without complications in case of new operations.

5 Claims, 2 Drawing Sheets

SELF-LOCKING BONE-SHAFT PART

This invention concerns a shaft-part implantable into a tubular bone for use in a joint-end prosthesis or as a bone-shaft replacement.

A large number of shaft parts for joint-end prostheses used in uncemented implants are known which require automatically locking the shaft in the marrow cavity. As an illustration, the patent document WO 86/06954 discloses a hip-prosthesis shaft with medial and lateral legs joined to one another by link structures. The shaft enlarges its cross-section upon bending stress and thereby fastens the shaft against the marrow cavity. Even though this and similar systems of the state of the art do clamp the shaft, the contact with the bone always remains restricted to three points. But these point contacts entail high local stresses.

The object of the invention is palliation. Its purpose is to create a self-locking shaft-part for a joint-end prosthesis of which the surface lends itself to making a real contacts with the bone so that the local stresses shall be relatively slight.

The invention solves this problem by means of a shaft-part evincing the features of claim 1.

Essentially the advantages offered by the invention are that, because of the shaft-part construction, maximum adaptation of the shaft surface to the anatomy of the marrow cavity is achieved and that both implantation and removal of the shaft-part can be carried out rapidly and without complications.

Because of the open and preferably frusto-conical design of the shaft, the marrow cavity remains open—contrary to the case of conventional systems—so that the bone maintains its blood circulation and bone metaplasia continues.

Another advantage lastly is that because the shaft cross-section is essentially circularly or elliptically symmetric, any rotational forces—of the kind that predominantly arise in a rapid, intermittent manner in hip prostheses—are significantly better absorbed and shunted in comparison to the mostly leaf-like shafts of the state of the art.

The drawing shows an illustrative embodiment of the invention and also elucidates the principle of operation. Details are provided below.

Figure 3:
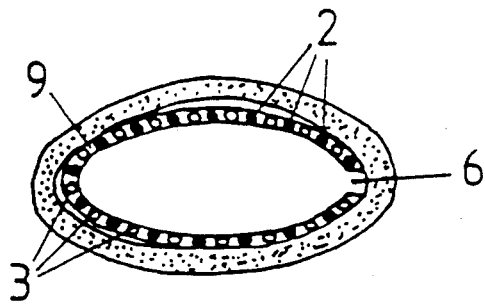
Figure 1:
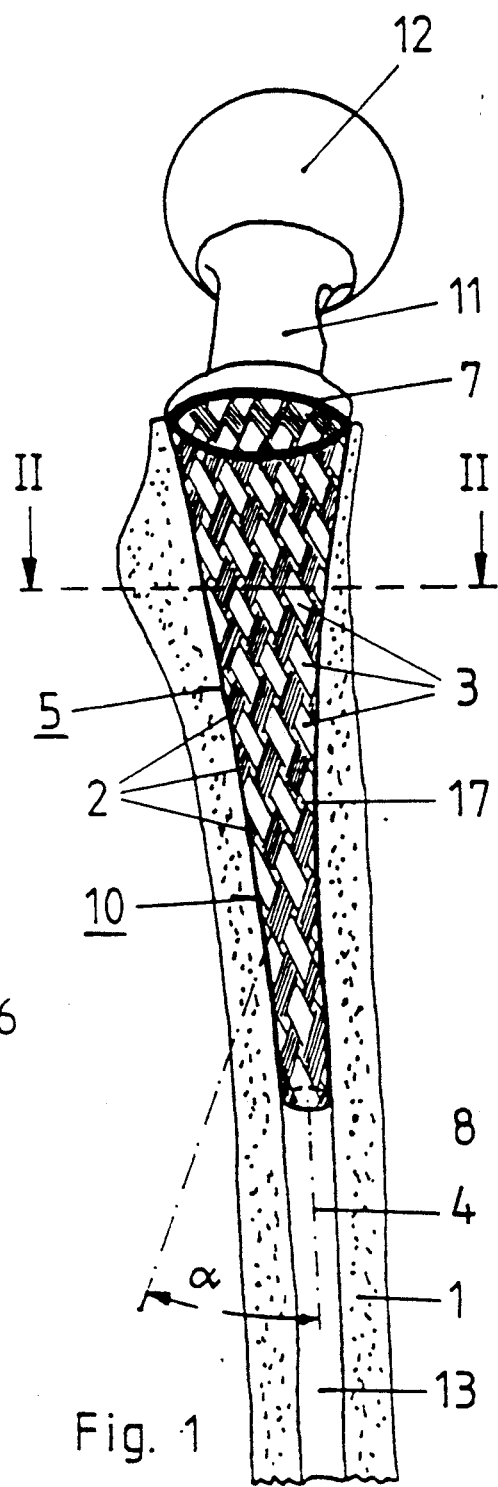
Figure 4:
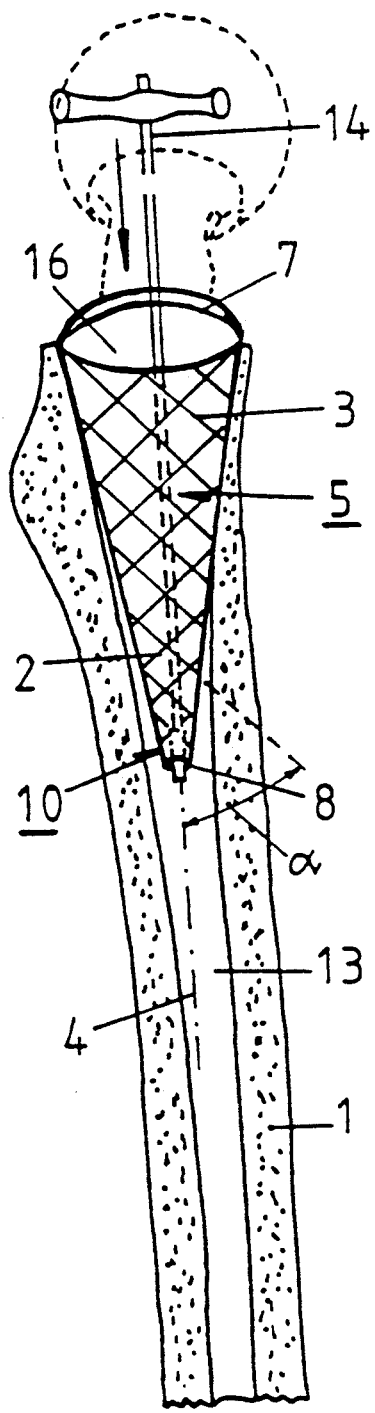
Figure 5:
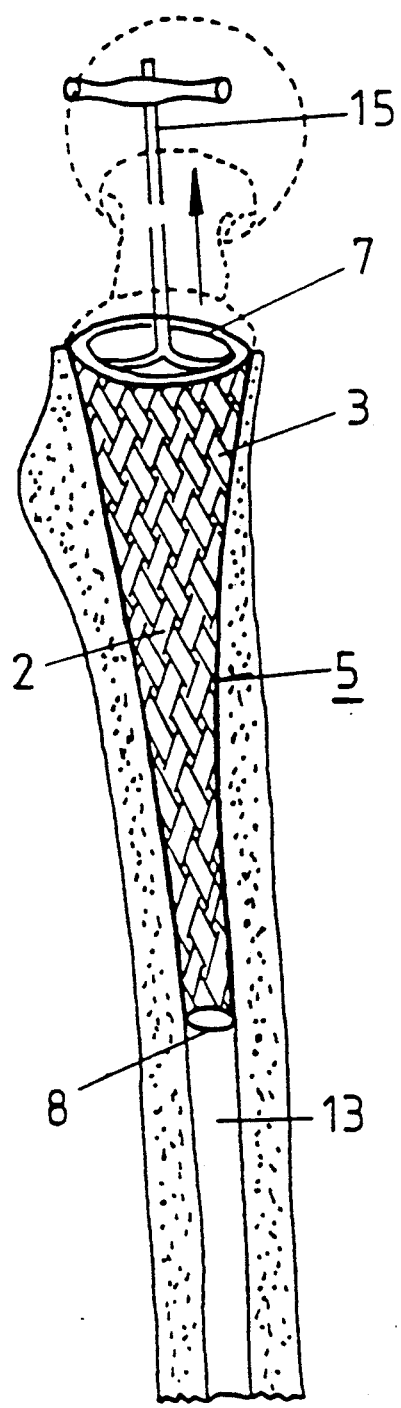

FIG. 1 is a lateral perspective of the shaft designed as the femur part of a hip prosthesis, FIG. 2 is a cross-section along line II—II of the shaft of FIG. 1, FIG. 3 is a cross-section in the manner of FIG. 2 of a longitudinally slotted shaft part of the invention, FIG. 4 is a perspective of the shaft part of the invention as yet not clamped, and FIG. 5 is a perspective of the clamped shaft part of the invention.

As shown by FIG. 1, the femur part designed as a hip prosthesis includes a frusto-conical braid 5 tapering from the proximal to distal ends in harmony with the anatomy of the marrow cavity and is constituted by two mutually crossing series of fibers 2, 3. Preferably the frusto-conical braid 5 assumes a nearly circular cross-section in the distal zone and a nearly elliptical cross-section in the proximal zone. As indicated in FIG. 1, the external contours of the braid 5 are longitudinally concave, i.e., the cross-section is narrower at the center than a regular frustrum of cone which would have straight outer contours. The fibers 2, 3 consist of a body-compatible metal, or of a suitable metal alloy or a plastic. Carbon fibers, illustratively of Pyrocarbon, are preferred. The fibers 2, 3 subtend an angle $\alpha$ to the longitudinal axis 4 of the hollow frustrum of cone formed by the braid 5. As a rule the angle $\alpha$ is about the same for both sets of fibers 2, 3. However, in order to achieve a better adaptation or fit of the braid in the proximal femur part, the angle $\alpha$ also may be variable along each fiber 2 or 3 and preferably becomes smaller from the distal toward the proximal zones.

In a preferred embodiment mode, the gaps 17 in the frusto-conical braid 5 made of fibers 2 and 3 are filled as shown in FIG. 2 with an elastomer 9 such as silicone rubber or Silastic in order to achieve a smooth shaft surface. This circumstance is significant because it has been found that newly formed bone material 1 easily grows into the coarse-structured surface of the bare braid 5, and removal of the shaft in the event of a new operation would thereby be seriously hampered.

As shown by FIG. 3, the frusto-conical braid 5 may comprise an axial slit 6 in a further and preferred embodiment mode.

The frusto-conical braid 5 comprises an annular member 7 in the proximal zone for fastening the proximal ends of the fiber sets 2 and 3, and an annular member 8 for fastening the distal ends of the fiber sets 2 and 3. These annular members 7, 8—which may be circular or elliptical—make it possible upon exertion of traction on one of the two rings with simultaneous fastening of the other ring to change the geometry of the braid 5 or of the hollow frustrum of cone formed thereby, in particular the length and the diameter of the shaft. This ability of the shaft part of the invention to be changed in shape leads to its application to implantation or removal of the prosthesis so outfitted and is discussed in detail below in relation to FIGS. 4 and 5.

The shaft part of the invention is implanted conventionally by inserting the shaft 10 into the marrow cavity 13 of the femur 1. As soon as the shaft 10 has attained a first and preliminary wedged position in the marrow cavity 13, then, as illustratively shown by FIG. 4, the distal annular structure 8 is engaged by a suitable long-stem instrument 14 and is further displaced distally by the application of axial pressure. In this process, tension is applied to the fibers 2, 3 that are fastened by their proximal ends to the annular member 7 fixed in the marrow cavity 13, and this tension results in an extension of the hollow, frusto-conical braid 5 with concurrent tapering. The angle $\alpha$ between the fibers 2 or 3 and the longitudinal axis 4 of the hollow frustrum of cone formed by the braid 5 then becomes less.

This stretching of the frusto-conical braid 5 allows attaining optimal contact with the marrow cavity 13 as shown in FIG. 1. This a real anchoring is retained even following implantation because any possibly "sinking" of the shaft would perforce lead to widening the frusto-conical braid 5.

The implantation instrument 14 is very easily handled because the frusto-conical braid 5 is open throughout, and therefore the tip of the implantation instrument 14 which is shaped to engage member 8 may be inserted directly through the inside space 16 of the frusto-conical braid 5 to engage the annular member 8.

Contrary to the case of the implanted shafts of the state of the art that are cemented or structured and cementless, the removal of the shaft part of the invention takes place in exceedingly simple manner. A suitable instrument 15 is designed to engage and seize the proximal annular member 7 and to pull it further proximally. In this procedure traction is exerted on the fibers 2, 3 which are fastened by their distal ends to the annular member 8 fixed in the marrow cavity 13, such that the hollow, frusto-conical braid 5 is extended while tapering. so that the shaft part easily detaches from the marrow cavity 13 and is removed from it.

I claim:

1. A shaft for an adaptable bone prosthesis comprising
    first and second sets of relatively movable fibers crossing each other and braided together to form a hollow, frusto-conical body having an adaptable length and an adaptable diameter, said body having a central axis, an outer surface, a proximal end and a distal end, said proximal end being larger than said distal end,
    said first and second sets of fibers each subtending an angle with said central axis of said body and wherein said angle is substantially the same for both sets of fibers;
    said body being dimensioned for insertion into a bone to form a joint-end prosthesis or bone shaft replacement and being adaptable to conform to the shape of the environment in which it is used.

2. A shaft for an adaptable bone prosthesis comprising
    first and second sets of relatively movable fibers crossing each other and braided together to form a hollow, frusto-conical body having an adaptable length and an adaptable diameter, said body having a central axis, an outer surface, a proximal end and a distal end, said proximal end being larger than said distal end, and
    means defining an axially extending slit through said body, said body being dimensioned for inserting into a bone to form a joint-end prosthesis or bone shaft replacement and being adaptable to conform to the shape of the environment in which it issued.

3. A shaft for an adaptable bone prosthesis comprising
    first and second sets of relatively movable fibers crossing each other and braided together to form a hollow, frusto-conical body having an adaptable length and an adaptable diameter, said body having a central axis, an outer surface, a proximal end and a distal end, said proximal end being larger tan said distal end, and
    a first annular end member, said distal ends of said fibers being attached to said end member;
    said body being dimensioned for insertion into a bone to form a joint-end prosthesis or bone shaft replacement and being adaptable to conform to the shape of the environment in which it is used.

4. A shaft according to claim 3 wherein said body further comprises a second annular end member, said proximal ends of said fibers being attached to said second end member.

5. A shaft according to claim 4 wherein longitudinal sections of said outer surface of said body have concave shapes.

* * * * *